(12) United States Patent
Cramail et al.

(10) Patent No.: US 10,047,171 B2
(45) Date of Patent: Aug. 14, 2018

(54) AMPHIPHILIC BIOCONJUGATES OBTAINED FROM XYLAN DERIVATIVES

(71) Applicants: UNIVERSITÉ DE BORDEAUX, Bordeaux (FR); Centre national de la recherche scientifique, Paris (FR); INSTITUT DES CORPS GRAS ETUDES ET RECHERCHES TECHNIQUES-ITERG, Pessac (FR); INSTITUT POLYTECHNIQUE DE BORDEAUX, Talence (FR); Institut Technologique FCBA, Grenoble (FR)

(72) Inventors: Henri Cramail, Sainte Terre (FR); Stéphane Jean-Pierre Albert Grelier, Parentis en Born (FR); Frédérique Pichavant, Gradignan (FR); Denilson Da Silva Perez, Pontacharra (FR); Carine Alfos, Pessac (FR); Maud Suzanne Chemin, Bordeaux (FR)

(73) Assignees: UNIVERSITÉ DE BORDEAUX, Bordeaux (FR); CENTRE NATIONAL DE LA RECHERCHE SCIENTIFIQUE, Paris (FR); INSTITUT DES CORPS GRAS ETUDES ET RECHERCHES TECHNIQUES-ITERG, Pessac (FR); INSTITUT POLYTECHNIQUE DE BORDEAUX, Talence (FR); INSTITUT TECHNOLOGIQUE FCBA, Grenoble (FR)

( * ) Notice: Subject to any disclaimer, the term of this patent is extended or adjusted under 35 U.S.C. 154(b) by 0 days.

(21) Appl. No.: 15/536,543

(22) PCT Filed: Dec. 16, 2015

(86) PCT No.: PCT/EP2015/080082
§ 371 (c)(1),
(2) Date: Jun. 15, 2017

(87) PCT Pub. No.: WO2016/097043
PCT Pub. Date: Jun. 23, 2016

(65) Prior Publication Data
US 2018/0002453 A1 Jan. 4, 2018

(30) Foreign Application Priority Data
Dec. 16, 2014 (EP) ..................... 14307052

(51) Int. Cl.
*C07H 3/06* (2006.01)
*C08B 37/00* (2006.01)
(Continued)

(52) U.S. Cl.
CPC .......... *C08B 37/0057* (2013.01); *A61K 47/38* (2013.01); *C07H 3/06* (2013.01);
(Continued)

(58) Field of Classification Search
None
See application file for complete search history.

(56) References Cited

U.S. PATENT DOCUMENTS

2012/0035340 A1* 2/2012 Slattegard ........... C08B 37/0057
527/312

OTHER PUBLICATIONS

Sunsanee Udomrati et al: "Esterified xylo-oligosaccharides for stabilization of Tween 80-stabilized oil-in-water emulsions: stabilization mechanism, rheological properties, and stability of emulsions", Journal of the Science of Food and Agriculture, vol. 94, No. 15, Apr. 30, 2014(Apr. 30, 2014), pp. 3241-3247, XP055193989, ISSN: 0022-5142, DOI: 10.1002/jsfa.6676 the whole document.

(Continued)

*Primary Examiner* — Traviss C McIntosh, III
(74) *Attorney, Agent, or Firm* — B. Aaron Schulman, Esq.; Stites & Harbison, PLLC

(57) ABSTRACT

The present invention concerns a compound of formula (I): wherein: —n is an integer comprised between 1 and 7; —$X_1$ is in particular a radical of formula —$CH_2$—S—$(CH_2)_k$—S—; —$A_1$ is in particular a linear or branched alkylene radical comprising from 2 to 30 carbon atoms, and —$X_2$ is in particular an alkoxy group of formula $OR_a$, wherein $R_a$ is a linear or branched alkyl group comprising from 1 to 10 carbon atoms.

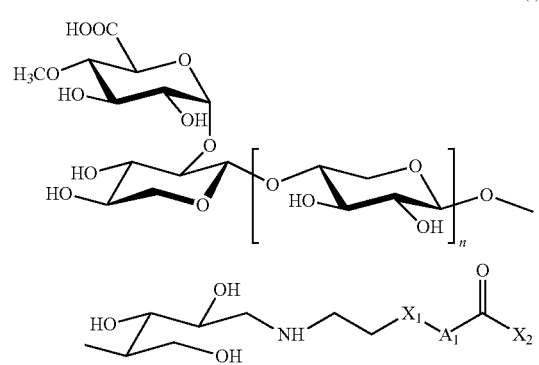

(I)

14 Claims, No Drawings

(51) Int. Cl.
  *C08L 5/14* (2006.01)
  *C08L 31/02* (2006.01)
  *A61K 47/38* (2006.01)

(52) U.S. Cl.
  CPC ............... *C08L 5/14* (2013.01); *C08L 31/02* (2013.01); *C08L 2201/06* (2013.01); *C08L 2205/02* (2013.01)

(56) References Cited

OTHER PUBLICATIONS

Bouxin F et al: "Direct conversion of xylan into alkyl pentosides", Carbohydrate Research, Pergamon, GB, vol. 345, No. 17, Nov. 22, 2010 (Nov. 22, 2010), pp. 2469-2473, XP027445294, ISSN: 0008-6215, DOI: 10.1016/J.CARRES.2010.09.003 [retrieved on Sep. 7, 2010] the whole document.
International Search Report for PCT/EP2015/080082, dated Mar. 16, 2016.
Written Opinion of the International Searching Authority for PCT/EP2015/080082, dated Mar. 16, 2016.
European Search Report for EP 14307052, completed Jun. 5, 2015.

* cited by examiner

AMPHIPHILIC BIOCONJUGATES OBTAINED FROM XYLAN DERIVATIVES

The present invention concerns new amphiphilic copolymers which are bioconjugates obtained from the conjugation of xylan derivatives and fatty acid derivatives.

The present invention also relates to the use of these bioconjugates in cosmetic, pharmaceutical and food compositions, in particular as surfactant.

The direction of the industry to renewable raw materials is a major challenge for which biomass offers promising perspectives. The chemical sector today begins a mutation from petrochemicals (petro-refinery) to agrochemicals (bio-refinery). Provided it does not compete with the food chain, agrochemicals offer original economic and ecological risk solutions, including reducing the carbon footprint and emissions of greenhouse gas emissions from finished products. Thus, alternative biomass is gradually integrating the chemical industry and in particular in the fuel sector. The challenge ahead is colossal; the aim is to produce bio-refinery by all the reaction intermediates and chemicals known to petrochemicals (mimicry), on the one hand, and to develop new molecules and bio-based materials, on the other hand. The partial deconstruction and direct modification of lignocellulosic biomass is also an important way to consider.

There is a growing interest in renewable resources, whether for energy or material appearance. In materials science, many natural resources have great potential for replacing fossil resources, including lignocellulosic biomass, mainly composed of polysaccharides. Especially, xylan is the most abundant hemicellulose in hardwoods. Xylans are a byproduct of the wood and paper industry, and are generally burned during regeneration of the reagents of the manufacturing process of pulp. However, because of their structures and properties, xylans are good candidates for the development of functional biomaterials.

The aim of the present invention is to provide new fully biobased and biocompatible bioconjugates.

Another aim of the present invention is to provide new amphiphilic polymers derived from xylans.

Another aim of the present invention is to provide biodegradable bioconjugates.

Therefore, the present invention relates to a compound of formula (I):

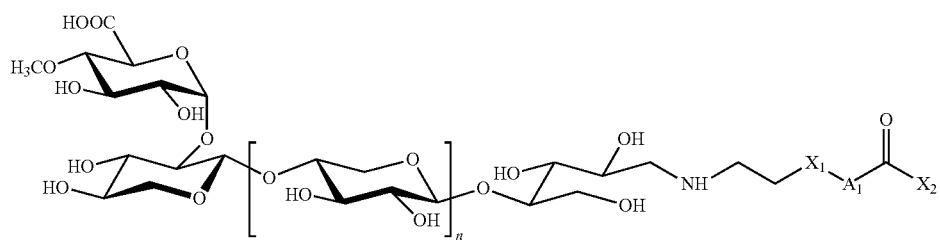

wherein:

n is an integer comprised between 1 and 15, preferably between 1 and 7, and more preferably between 2 and 6;

$X_1$ is chosen from the group consisting of:
a radical of formula (II):

wherein k is an integer comprised between 2 and 10, and
a radical of formula (III):

$A_1$ is chosen from the group consisting of:
a linear or branched alkylene radical $A'_1$, optionally substituted by at least one hydroxyl group, comprising from 2 to 30 carbon atoms, when $X_1$ is a radical of formula (II) as defined above, and a radical of formula -$A_2$-O—, wherein $A_2$ is a linear or branched alkylene radical, comprising from 2 to 10 carbon atoms, when $X_1$ is a radical of formula (III) as defined above, $X_2$ is chosen from the group consisting of:
an alkoxy group of formula $OR_a$, wherein $R_a$ is H or a linear or branched alkyl group comprising from 1 to 10 carbon atoms, when $X_1$ is a radical of formula (II) as defined above, and a linear or branched alkyl group $A_3$, optionally substituted by at least one hydroxyl group, optionally comprising at least one double bond, comprising from 2 to 30 carbon atoms, when $X_1$ is a radical of formula (III) as defined above.

The compounds of formula (I) are conjugates of xylan and fatty acid esters. They are obtained by the conjugation of xylan derivatives with fatty acid derivatives, through covalent binding.

The present invention also relates to a compound of formula (I-1):

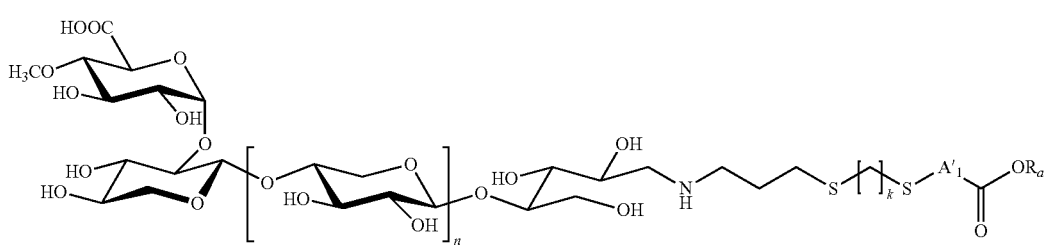
(I-1)

wherein n, k, $A'_1$ and $R_a$ are as defined in formula (I).

A compound of formula (I-1) corresponds to a compound of formula (I) wherein $X_1$ is a radical of formula (II) as defined above, $A_1$ is an alkylene radical $A'_1$ as defined above and $X_2$ is a group $OR_a$, $R_a$ being as defined above.

According to an embodiment, in formula (I-1), n is 3.

According to an embodiment, in formula (I-1), $A'_1$ has the formula (IV):

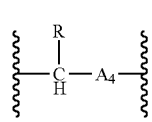
(IV)

wherein:
R is a linear or branched alkyl group comprising from 2 to 15 carbon atoms, and optionally comprising at least one hydroxyl group; and
$A_4$ is a linear or branched alkylene radical comprising from 2 to 15 carbon atoms.

Preferably, in formula (I-1), $A'_1$ has the following formula (IV-1):

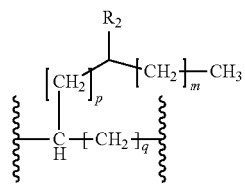
(IV-1)

wherein:
$R_2$ is H or OH;
p, m, and q are integers comprised between 2 and 10.

More preferably, $A'_1$ has the following formula (IV-2):

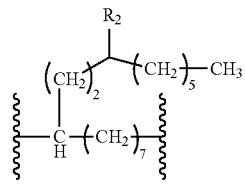
(IV-2)

$R_2$ being as defined above in formula (IV-1).

According to a preferred embodiment, in formula (I-1), $R_a$ is a methyl group.

Preferred compounds of formula (I-1) have the following formula:

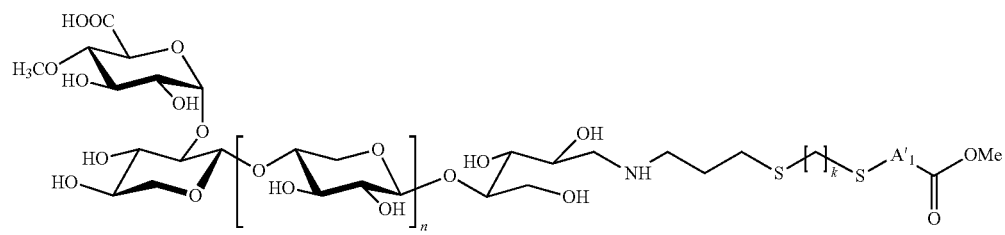

n being preferably 4.

According to a preferred embodiment, in formula (I-1), k is 2.

According to a preferred embodiment, in formula (I-1), k is 2 and $R_a$ is methyl. Such compounds have the following formula:

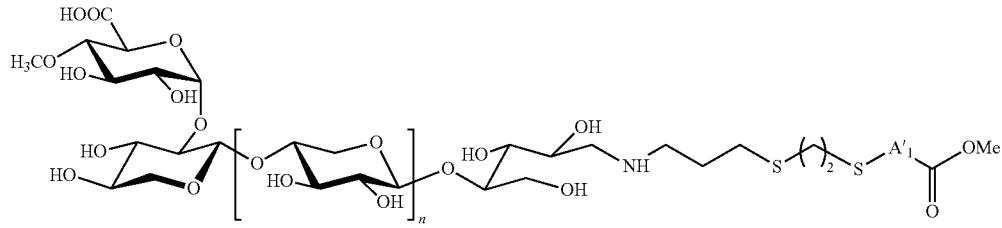

n being preferably 4.

According to an embodiment, preferred compounds of formula (I-1) have the following formula:

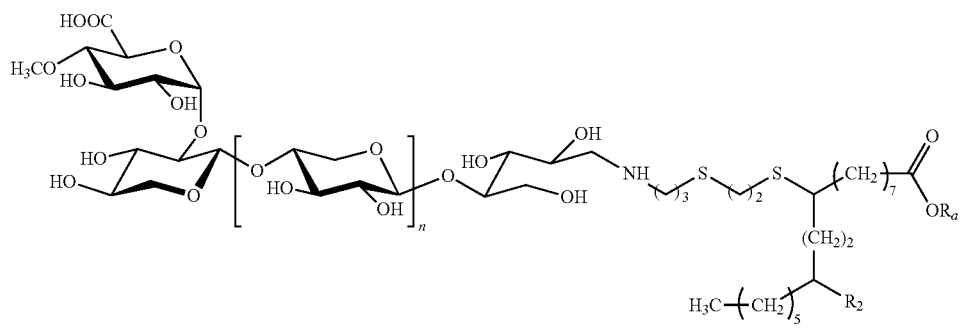

n, $R_a$ and $R_2$ being as defined above.

More particularly, the present invention relates to the following compounds:

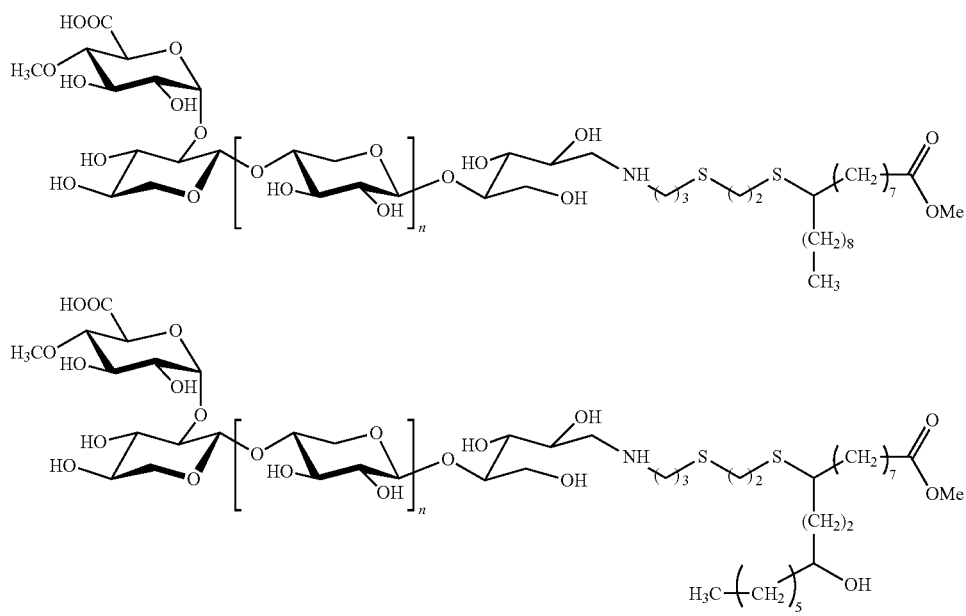

The present invention also relates to a process for the preparation of a compound of formula (I-1) as defined above, comprising the reaction of a compound of formula (VI):

with a compound of formula (VI):

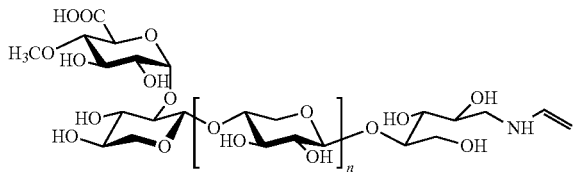

with a compound of formula (VII):

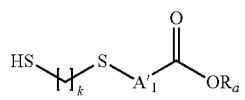

k, n, A'₁ and R_a being as defined in formula (I-1).

This process consists in a thiol-ene coupling.

According to an embodiment, the compounds of formula (VI) are prepared by reductive amination of xylooligosaccharides of formula (X) through the following reaction scheme:

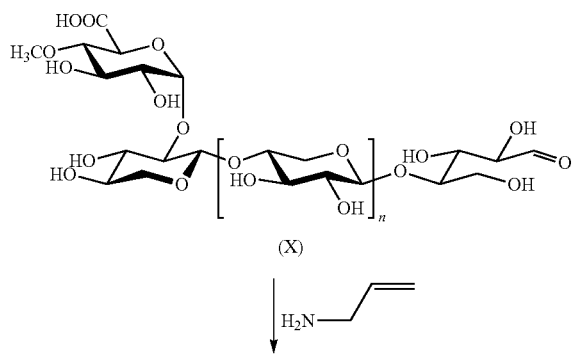

-continued

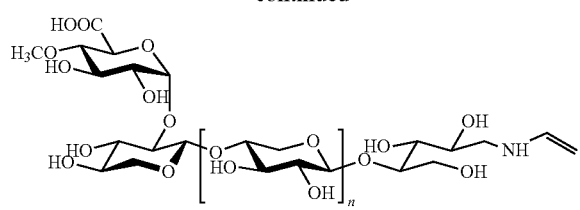

This functionalization reaction is carried out with reactions well-known in the art.

The compounds of formula (X) are prepared according to a well-known reaction for polysaccharides named reductive amination from beechwood 4-O-methylglucuronoxylan.

According to an embodiment, the compounds of formula (VII) are prepared by thiol functionalization of esters of fatty acids, according to well-known reactions.

Especially, such compounds may be obtained by reacting a dithiol of formula (XI):

k being as defined above, with a fatty acid derivative having the following formula (XII):

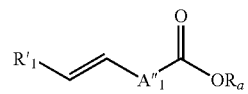

wherein:

A''₁ represents a bond or a linear or branched alkylene radical, having from 1 to 18, preferably from 1 to 10, carbon atoms, said alkylene radical optionally comprising at least a double bond, and/or optionally substituted by at least one hydroxyl group;

R'₁ is a hydrogen or an alkyl group, straight or branched, having from 1 to 15, preferably from 1 to 8, carbon atoms; and R_a is as defined above.

The present invention also relates to a compound of formula (I-2):

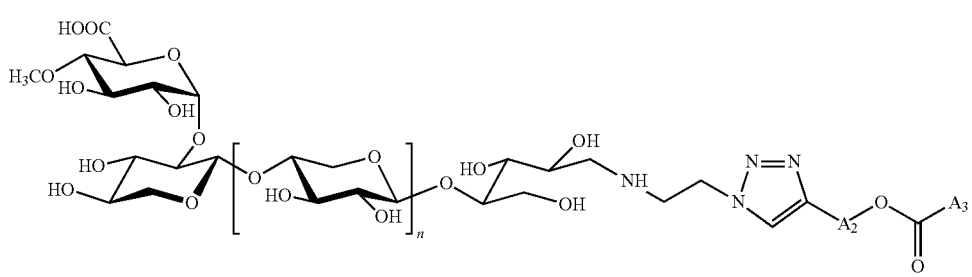

wherein n, A₂ and A₃ are as defined in formula (I).

A compound of formula (I-2) corresponds to a compound of formula (I) wherein X₁ is a radical of formula (III) as defined above, A₁ is a radical -A₂-O— as defined above and X₂ is an alkyl group A₃ as defined above.

According to an embodiment, in formula (I-2), n is 3.

According to an embodiment, in formula (I-2), A₃ has the formula (V):

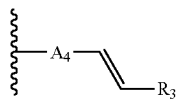

(V)

wherein:
$R_2$ is H or OH;
r, s, and t are integers comprised between 2 and 10.
More preferably, $A_3$ has the following formula (V-2):

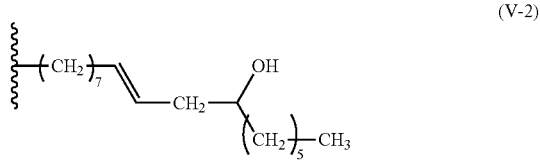

(V-2)

wherein:
$A_4$ is a linear or branched alkylene radical comprising 1 to 10 carbon atoms, optionally substituted by at least one hydroxyl group, and
$R_3$ is a linear or branched alkyl group comprising 1 to 10 carbon atoms, optionally substituted by at least one hydroxyl group.

Preferably, $A_3$ has the following formula (V-1):

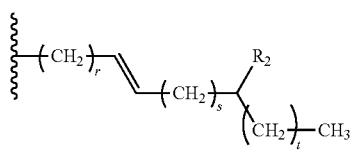

(V-1)

According to a preferred embodiment, in formula (I-2), $A_2$ is an ethylene radical.

Preferred compounds of formula (I-2) have the following formula:

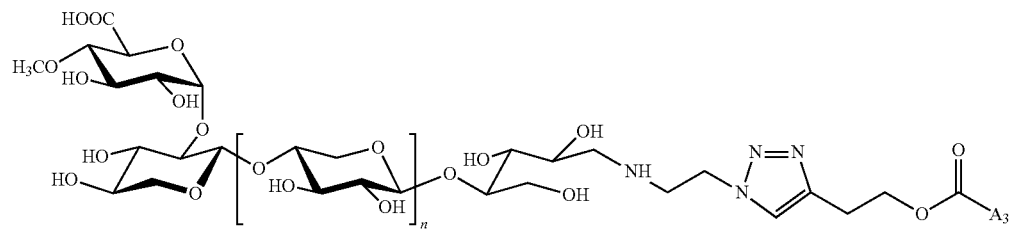

n being preferably 4.

According to an embodiment, preferred compounds of formula (I-2) have the following formula:

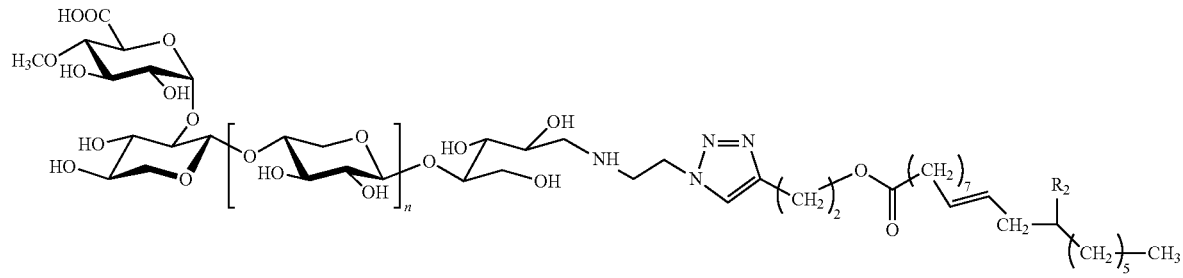

n and $R_2$ being as defined above.

More particularly, the present invention relates to the following compounds:

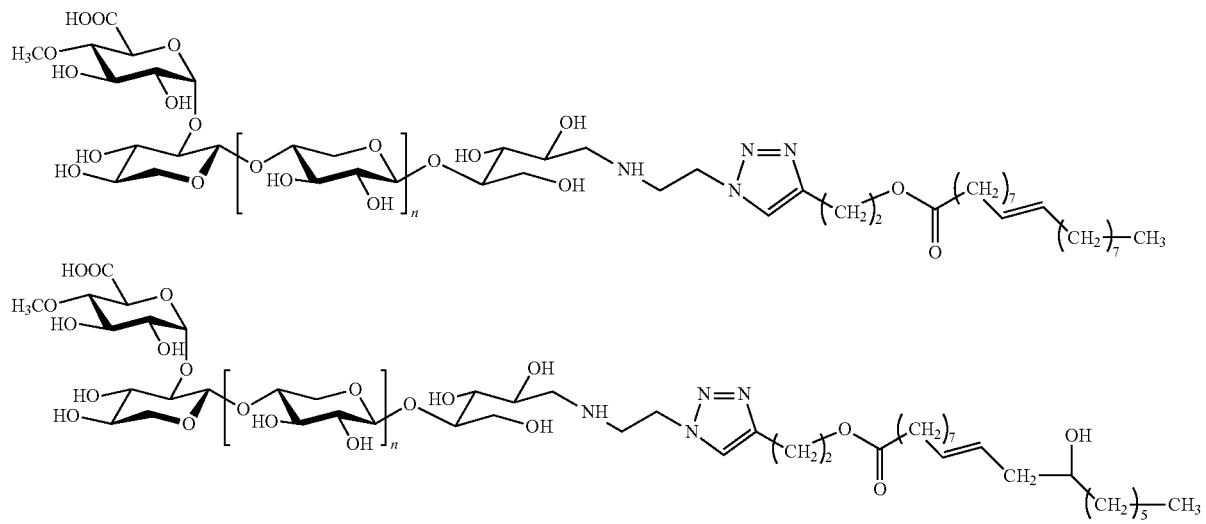

The present invention also relates to a process for the preparation of a compound of formula (I-2) as defined above, comprising the reaction of a compound of formula (VIII):

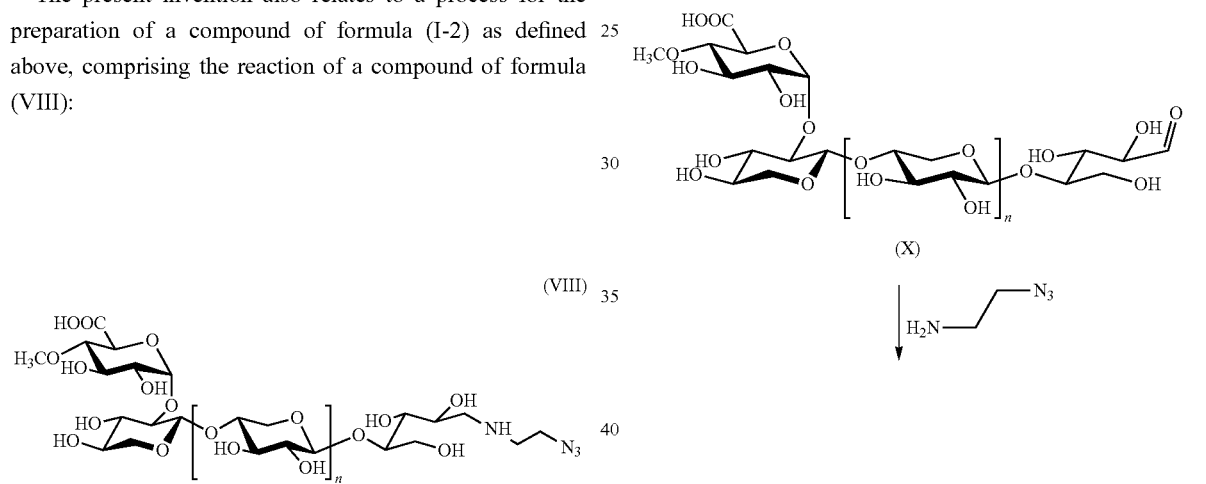

with a compound of formula (IX):

(IX)

n, $A_2$, and $A_3$ being as defined in formula (I-2).

This process consists in an azide-alcyne coupling.

According to an embodiment, the compounds of formula (VIII) are prepared by reductive amination of xylooligosaccharides of formula (X) through the following reaction scheme:

This functionalization reaction is carried out with reactions well-known in the art.

According to an embodiment, the compounds of formula (IX) are prepared by alcyne functionalization of esters of fatty acids, according to well-known reactions.

Especially, such compounds may be obtained by reacting an alcyne of formula (XIII):

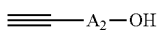

$A_2$ being as defined in formula (I-2),
with an ester of fatty acid of formula (XIV):

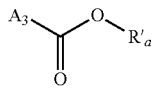

wherein:
$A_3$ is as defined in formula (I-2); and
$R'_a$ is a linear or branched alkyl group comprising from 1 to 10 carbon atoms, being preferably methyl.

As used herein, the term "$(C_x$-$C_y)$alkyl" means a saturated aliphatic hydrocarbon group, which may be straight or branched, having x to y carbon atoms in the chain. Preferred alkyl groups have 1 to about 30, in particular 1 to 12, more particularly 1 to 15, preferably 1 to 10, and more preferably 1 to 6, carbon atoms in the chain. The following alkyl groups may be cited as example: methyl, ethyl, propyl, butyl, pentyl, hexyl, heptyl, octyl, nonyl, decyl, dodecyl.

Within the present application, the alkyl groups may also be substituted by one or several hydroxyl groups.

Within the present application, the alkyl groups may also comprise one or several insaturations. When they comprise a double bond, these alkyl groups may also be called "alkenyl" groups.

As used herein, the term "$(C_x$-$C_y)$alkylene" (or "alkylidene") refers to a divalent saturated aliphatic hydrocarbon radical, comprising from x to y carbon atoms, having preferably from 1 to 30, in particular 1 to 15 carbon atoms, more particularly 1 to 12 carbon atoms and more preferably 2 to 10 carbon atoms. When said radical is linear, it may be represented by the formula $(CH_2)_m$ wherein m is an integer varying from 1 to 30, in particular from 1 to 15, more particularly from 1 to 12, and preferably from 2 to 10. The following alkylene may be cited as example: methylene, ethylene, propylene, butylene, pentylene, hexylene, heptylene, octylene, nonylene, decylene, dodecylene.

Within the present application, the alkylene radicals may also be substituted by one or several hydroxyl groups.

Within the present application, the alkylene radicals may also comprise one or several insaturations. When they comprise a double bond, these alkylene radicals may also be called "alkenylene" radicals.

As used herein, the term "alkoxy" means an alkyl-O— group wherein the alkyl group is as herein described. Exemplary alkoxy groups include methoxy, ethoxy, n-propoxy, i-propoxy, n-butoxy and heptoxy.

Surprisingly, the compounds of the invention have surfactant properties. Especially, the inventors have discovered that these compounds have properties similar to the well-known surfactant Tween® 80.

Therefore, the present invention also relates to compositions, such as detergent compositions, comprising at least one compound of formula (I) as defined above, in particular at least one compound of formula (I-1) as defined above and/or at least one compound of formula (I-2) as defined above.

The present invention also relates to the use of a compound of formula (I) as defined above, in particular of formula (I-1) as defined above or of formula (I-2) as defined above, as a surfactant.

According to another embodiment, the present invention relates to a cosmetic composition comprising at least one compound of formula (I) as defined above and a physiologically acceptable vehicle.

The present invention also relates to a pharmaceutical composition comprising at least one compound of formula (I) as defined above and a pharmaceutically acceptable excipient.

The present invention also relates to a food supplement comprising at least one compound of formula (I) as defined above.

The present invention also relates to the use of a compound of formula (I) as defined above, in particular of formula (I-1) as defined above or of formula (I-2) as defined above, for the encapsulation of actives. Indeed, it has been shown that the compounds of the invention are able to self-assemble.

In the whole application, the wording «comprising one» or «including one» means «comprising at least one» or «including at least one» unless specified otherwise.

The invention is described in the foregoing by way of non-limiting examples.

EXAMPLES

Example 1: Preparation of Xylooligosaccharides

Controlled sulfuric acidic hydrolysis of beechwood 4-O-methylglucuronoxylan (MGX) was performed to get well-defined xylooligosaccharides (XOS).

MGX (Sigma Aldrich; X-4252) was solubilized in sulfuric acidic media (0.7 M) at 50 g/L. The solution was heated at 90° C. for 45 minutes under magnetic stirring. After reaction, the solution was cooled down with ice and neutralized using a saturated barium hydroxide solution. Finally, centrifugation was conducted to remove the salt that precipitated and the supernatant was freeze-dried. XOS were purified by selective ethanol purification (1:9). The purification was done twice before drying the precipitate under vacuum.

XOS were obtained with 22 wt. % yield and characterized to have around 6 xylose units and only one methylglucuronic acid (MeGlcA) unit per chain positioned at the non reductive end chain.

Example 2: XOS Functionalization by Reductive Amination

XOS were dissolved in deionized water at 100 g/L.
2-aminoethylazide (prepared from 2-chloroethylamine as explained below) or allylamine (Alfa Aesar) (7.5 eq.) was added under magnetic stirring, followed by $NaBH_3CN$ (Sigma Aldrich) (7.5 eq.).

Preparation of 2-aminoethylazide 2-chloroethylamine hydrochlorate (Sigma Aldrich) is solubilized in water (133 g/L) at 80° C. Then sodium azide (3 eq., Sigma Aldrich) is added and the mixture is kept under reflux and magnetic stirring for the night. The mixture is cooled to room temperature then to 0° C. using an ice bath. Potassium hydroxide (same amount as 2-chloroethylamine hydrochlorate, Prolabo) is added and after total dissolution, the product is extracted using diethyl ether. Organic phase is dried over magnesium sulfate (Acros Organics), filtered and finally evaporated to obtain 2-aminoethylazide (20 mol. % yield).

The mixture XOS+2-aminoethylazide or allylamine was stirred at 50° C. for three days. The solution was then precipitated in ethanol three times (1:10) to remove the excess of amine and NaBH$_3$CN. The product was finally dried under vacuum (random yield between 40 and 80 wt. % due to the purification step).

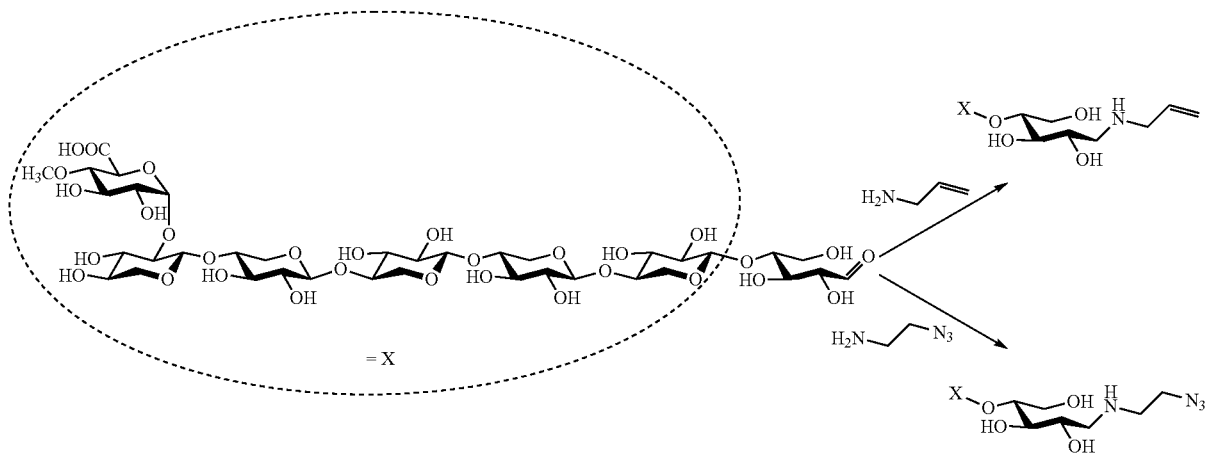

Example 3: Thiol Functionalization of Fatty Acid Esters

Fatty acid esters (FAE) were dissolved in MeOH at 50 g/L. The esters used here are the following: methyloleate (MeOl) (Alfa Aesar) and methylricinoleate (MeRic) (Nu-Chek Prep).

Ethanedithiol (20 eq, Acros Organics) was added under magnetic stirring, followed by DMPA (0.1 eq.) (Sigma Aldrich). The mixture was stirred under UV irradiation for 15 minutes. The solution was then dried under vacuum. Finally the mixture was purified using flash chromatography (gradient of dichloromethane and methanol) and dried under vacuum (88 wt. % yield).

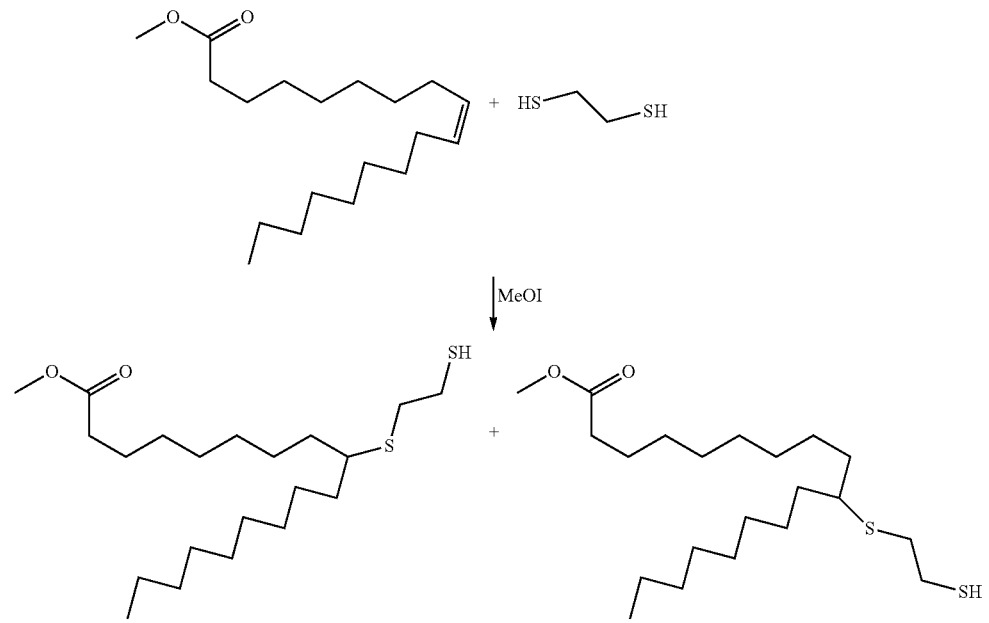

-continued

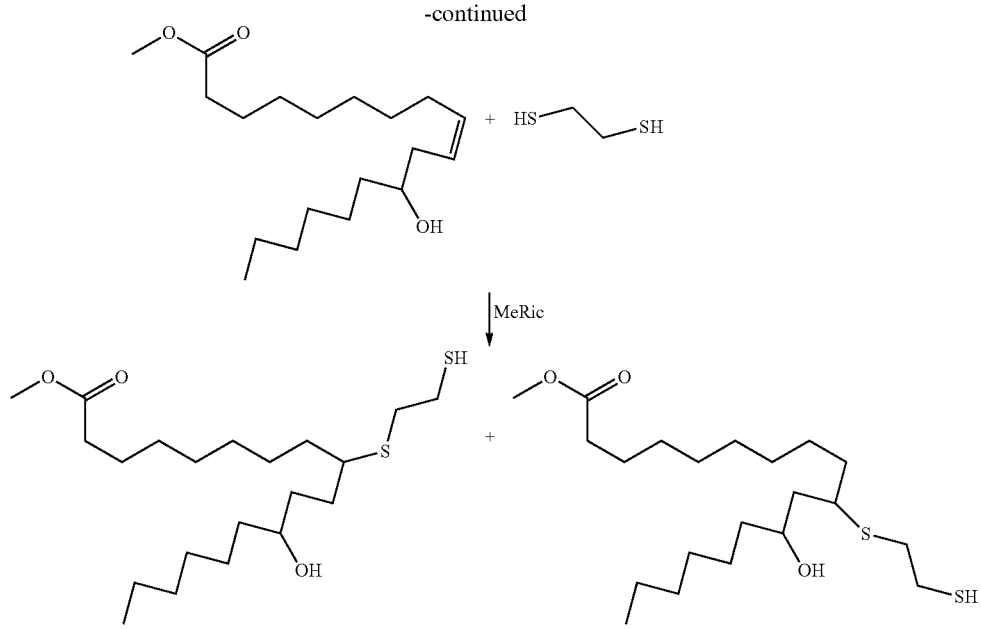

Example 4: Thiol-Ene (TE) Coupling

Functionalized XOS were dissolved in MeOH at 50 g/L the day before to ensure solubilization. Functionalized FAE (15 eq.) and DMPA (0.75 eq.) were added under magnetic stirring in five times every hour while the mixture was stirred under UV irradiation. The mixture was stirred under UV irradiation for 19 hours, i.e. total reaction time of 24 h. The solution was then dried under vacuum. Finally the mixture was purified by washing the mixture two times with EtOH and one time with cyclohexane (72 wt. % yield).

with Oleate:

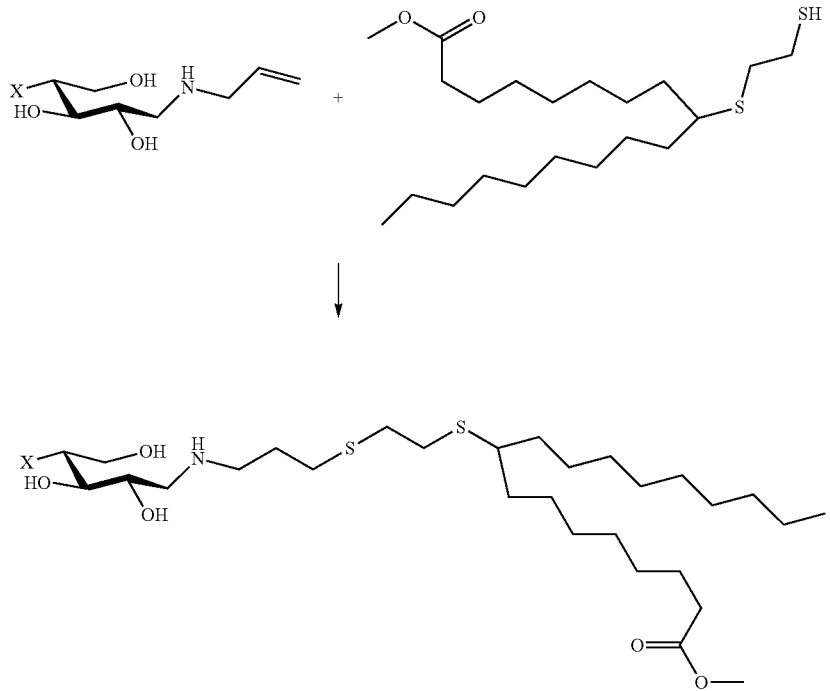

with Ricinoleate:

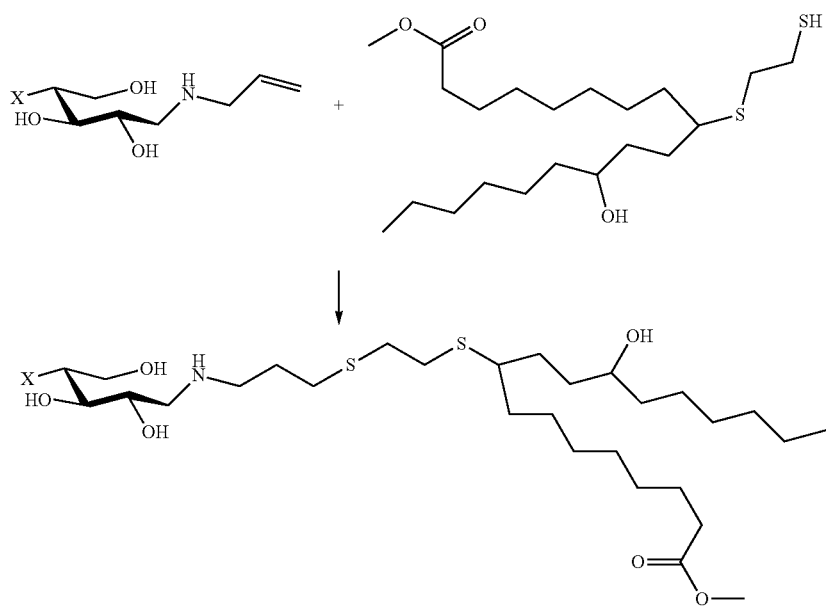

These TE bioconjugates have been analyzed through NMR, TGA and DSC. NMR analyses were performed in D$_2$O as well as in CDCl$_3$.

In deutered water, one can clearly see the well-defined signals of XOS between 2.8 and 6.1 ppm.

In deutered chloroform, one can barely see signals from MeOI. Most of bioconjugates have precipitated at the bottom of the NMR tube.

Then, thermal properties of TE bioconjugates were analyzed though TGA and DSC. TGA chromatograms clearly show that thermal stability of TE bioconjugates is increased in comparison to XOS. This increase can be due to the presence of sulfur. The temperature stability shows that the coupling is effective.

Example 5: Alcyne Functionalization of FAE

FAE were functionalized in bulk using 3-butyn-1-ol (10 eq., Acros Organics) with TBD as catalyst (0.1 eq., Sigma Aldrich). The mixture was stirred under nitrogen at 100° C. for 4 hours and for 4 hours more at 100° C. under vacuum. The mixture was then purified by adding ethyl acetate and water (4:1). The organic phase is mixed with water two times more and dried over Na$_2$SO$_4$. Finally the organic phase is filtrated and evaporated (75 wt. % yield).

with Oleate:

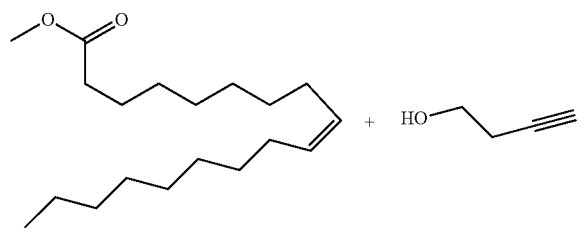

-continued

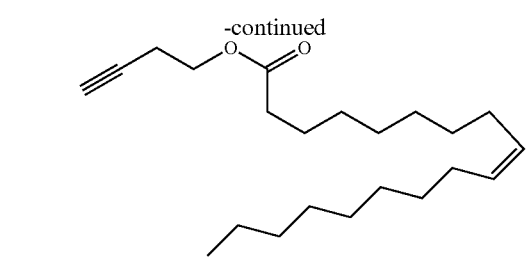

with Ricinoleate:

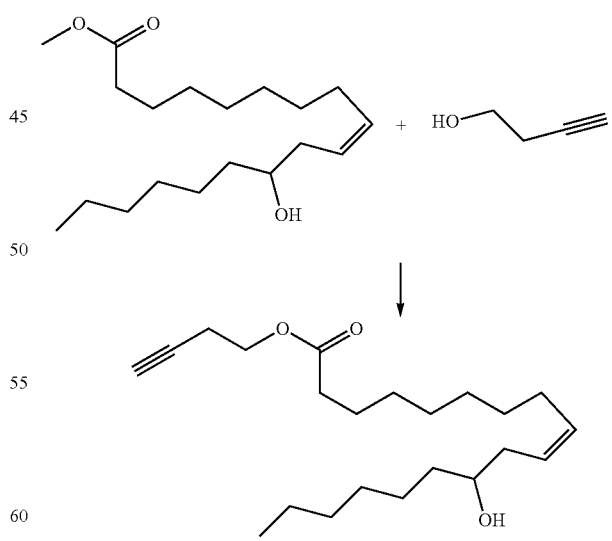

Example 6: Azide-Alcyne (AA) Coupling

XOS were dissolved in DMSO at 100 g/L and stirred for at least few hours in a water bath at 30° C. FAE derivatives (1 eq.) were dissolved in DMSO (volume as low as possible)

and added to the solution. After 15 minutes stirring, sodium ascorbate (NaAsc) (3.5 eq) was added. Finally after 10 minutes, $CuSO_4$ (3.5 eq.) was added. The solution was stirred for 20-25 hours at 30° C. The reaction medium was then dialyzed 4-5 days against milliQ water (100-500 Da membrane) containing EDTA (VWR International) the first 2 days, and finally lyophilized (29 wt. % yield).

with Oleate:

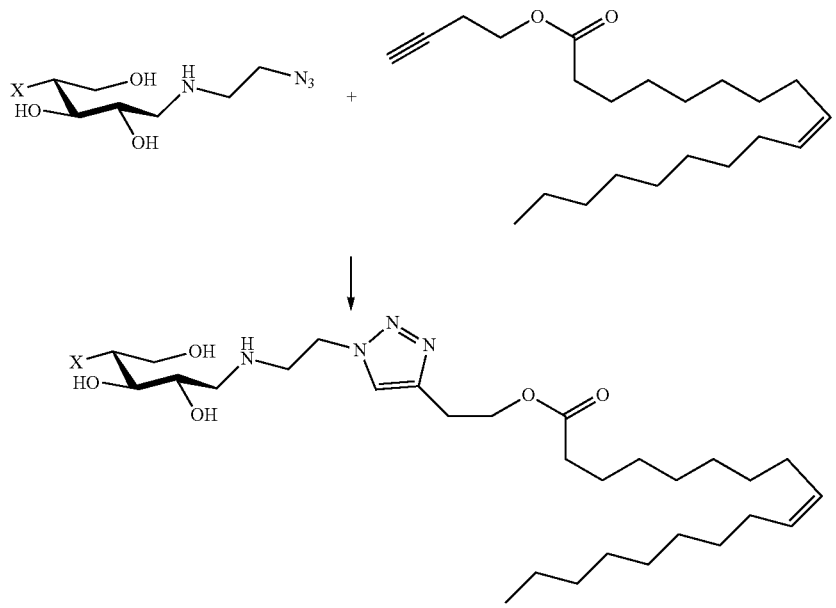

Analyses of bioconjugates clearly show the disappearance of the $N_3$ vibration (2,110 $cm^{-1}$) meaning that the coupling was effective and that the conversion seems full.

Spectra also show the appearance of C=O (1730 $cm^{-1}$) and C—N (1380 $cm^{-1}$) vibrations due to the Huisgen cycloaddition and the appearance of clear signals corresponding to $CH_2$ vibrations (asymmetric vibrations at 2,920 $cm^{-1}$ and symmetric ones at 2,650 $cm^{-1}$) of FAE. Then, NMR analyses were performed in $D_2O$ as well as $CDCl_3$ for both bioconjugates.

In deutered water—for both bioconjugates—one can clearly see the signals of XOS between 3.1 and 4.7 ppm but with Ricinoleate:

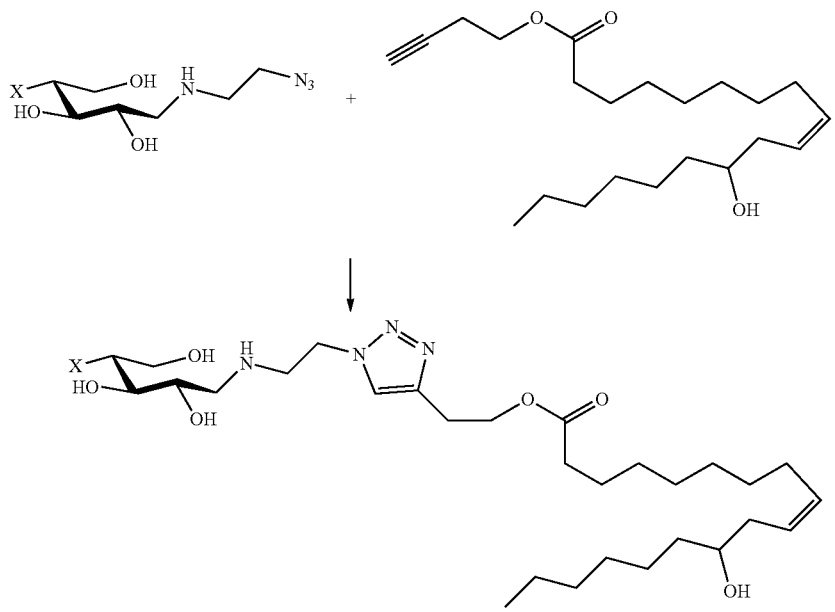

AA bioconjugates have been analyzed through the same techniques as TE ones, i.e. NMR, TGA and DSC. Moreover, AA bioconjugates were also analyzed through IR spectroscopy.

the signals of FAE are undefined between 0.6 and 1.8 ppm. Moreover, no signal from aminoethylazide can be seen, confirming, together with IR, that the conversion is full.

In deutered chloroform—for both bioconjugates—one can see signals from FAE only. Some bioconjugates have precipitated at the bottom of the NMR tube but most of them are left in solution and organized in chloroform with FAE at the outer of the objects.

Finally, thermal properties of these AA bioconjugates were analyzed though TGA and DSC. For both FAE, TGA chromatograms show that thermal stability of AA bioconjugates is similar to XOS.

For both FAE, DSC chromatograms show a flat profile for AA bioconjugates as well as for XOS. Because FAE still have a crystallization/fusion behavior after functionalization, it means that there is no free FAE left in the product.

Example 7: Self-Assembly of Copolymers Obtained Using AA Coupling

The obtained copolymers are amphiphilic with a HLB of 15 (Davies method). This HLB value is similar to the one of Tween® 80, a surfactant widely employed in cosmetic and food fields.

The CMC of XOS-AA-Ric has been measured equal to 100 mg/L and the one of XOS-AA-OI equal to 260 mg/L. These copolymers decrease interface tension (water/air) as well as Tween® 80 and increase the wetting of aqueous solution on several surfaces as PET and PTFE. Moreover, XOS-AA-Ric has a foaming capacity. These results promise potential applications as surfactant in cosmetic and food industries.

Moreover, objects of XOS-AA-Ric and XOS-AA-OI self-assembly were characterized by DLS and TEM: spherical objects are formed with a micellar size under 50 nm. These objects have the fatty chains in their core and the XOS forming the shell. These objects are in dynamic equilibrium. Aggregates (≈500 nm) are also formed and can be eliminated by a simple filtration at 0.45 µm. Interestingly, their assembly is reversible and XOS-AA-Ric and XOS-AA-OI can self-assemble in chloroform forming spherical objects with a micellar size under 50 nm. In that case, XOS are in the core of the objects and fatty chains form the shell. These objects are also in dynamic equilibrium and bigger aggregates (≈1000 nm) are formed and can be eliminated by a simple filtration at 0.45 µm.

These results promise potential applications in active substance delivery as these polymers are biocompatible and biodegradable.

The invention claimed is:

1. A compound of formula (I):

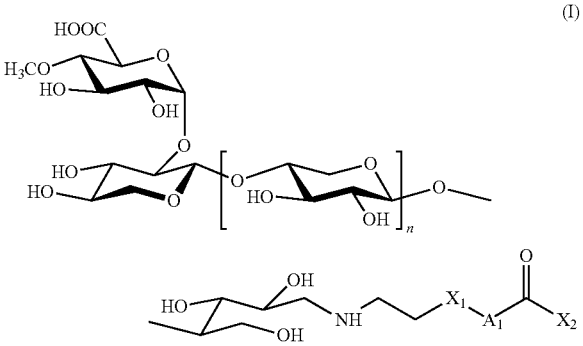

wherein:

n is an integer comprised between 1 and 15;

$X_1$ is chosen from the group consisting of:

a radical of formula (II):

$$-CH_2-S-(CH_2)_k-S- \quad (II)$$

wherein k is an integer comprised between 2 and 10, and a radical of formula (III):

$A_1$ is chosen from the group consisting of:

a linear or branched alkylene radical $A'_1$, optionally substituted by at least one hydroxyl group, comprising from 2 to 30 carbon atoms, when $X_1$ is a radical of formula (II) as defined above, and a radical of formula -$A_2$-O—, wherein $A_2$ is a linear or branched alkylene radical, comprising from 2 to 10 carbon atoms, when $X_1$ is a radical of formula (III) as defined above, $X_2$ is chosen from the group consisting of:

an alkoxy group of formula $OR_a$, wherein $R_a$ is H or a linear or branched alkyl group comprising from 1 to 10 carbon atoms, when $X_1$ is a radical of formula (II) as defined above, and a linear or branched alkyl group $A_3$, optionally substituted by at least one hydroxyl group, optionally comprising at least one double bond, comprising from 2 to 30 carbon atoms, when $X_1$ is a radical of formula (III) as defined above.

2. The compound of claim 1, of formula (I-1):

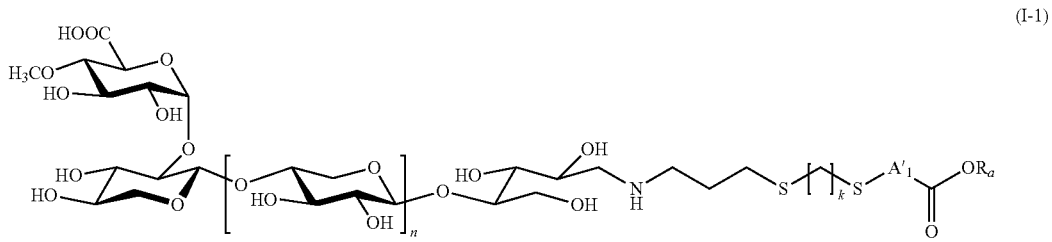
(I-1)

wherein n, k, $A'_1$ and $R_a$ are as defined in claim 1.

3. The compound of claim 1, of formula (I-2):

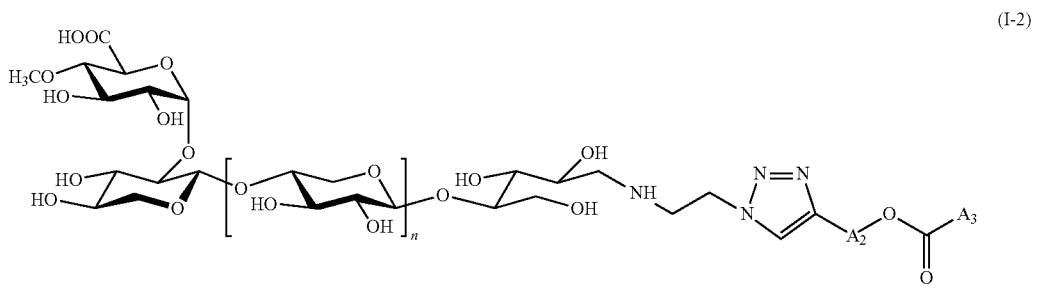
(I-2)

wherein n, $A_2$ and $A_3$ are as defined in claim 1.

4. The compound of claim 2, wherein $A'_1$ has the formula (IV):

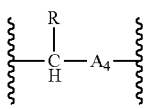
(IV)

wherein:
R is a linear or branched alkyl group comprising from 2 to 15 carbon atoms, and optionally comprising at least one hydroxyl group; and
$A_4$ is a linear or branched alkylene radical comprising from 2 to 15 carbon atoms.

5. The compound of claim 3, wherein $A_3$ has the following formula (V):

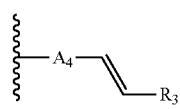
(V)

wherein:
$A_4$ is a linear or branched alkylene radical comprising 1 to 10 carbon atoms, optionally substituted by at least one hydroxyl group, and
$R_3$ is a linear or branched alkyl group comprising 1 to 10 carbon atoms, optionally substituted by at least one hydroxyl group.

6. The compound of claim 1, having one of the following formulae:

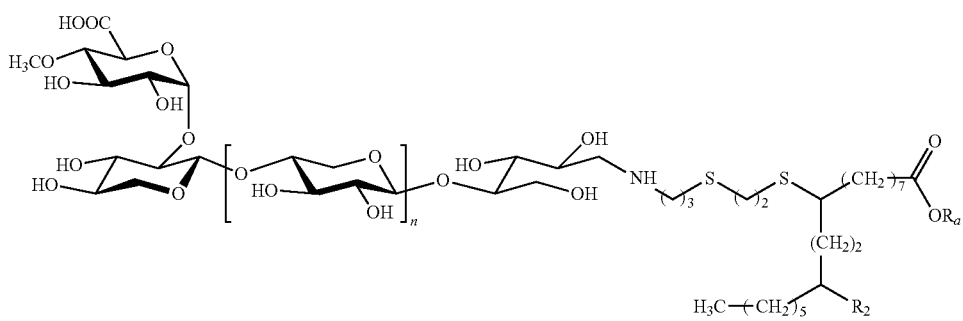

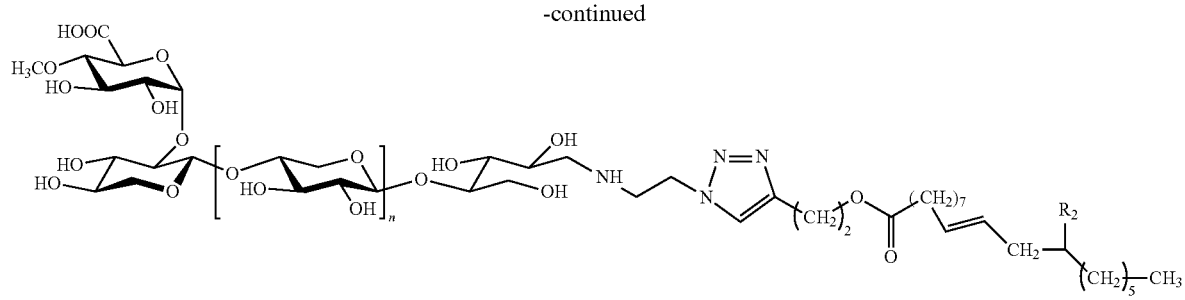
wherein:
$R_2$ is H or OH; and
$R_a$ is as defined in claim 1.
7. The compound of claim 1, wherein n is 3.
8. The compound of claim 1, having one of the following formulae:
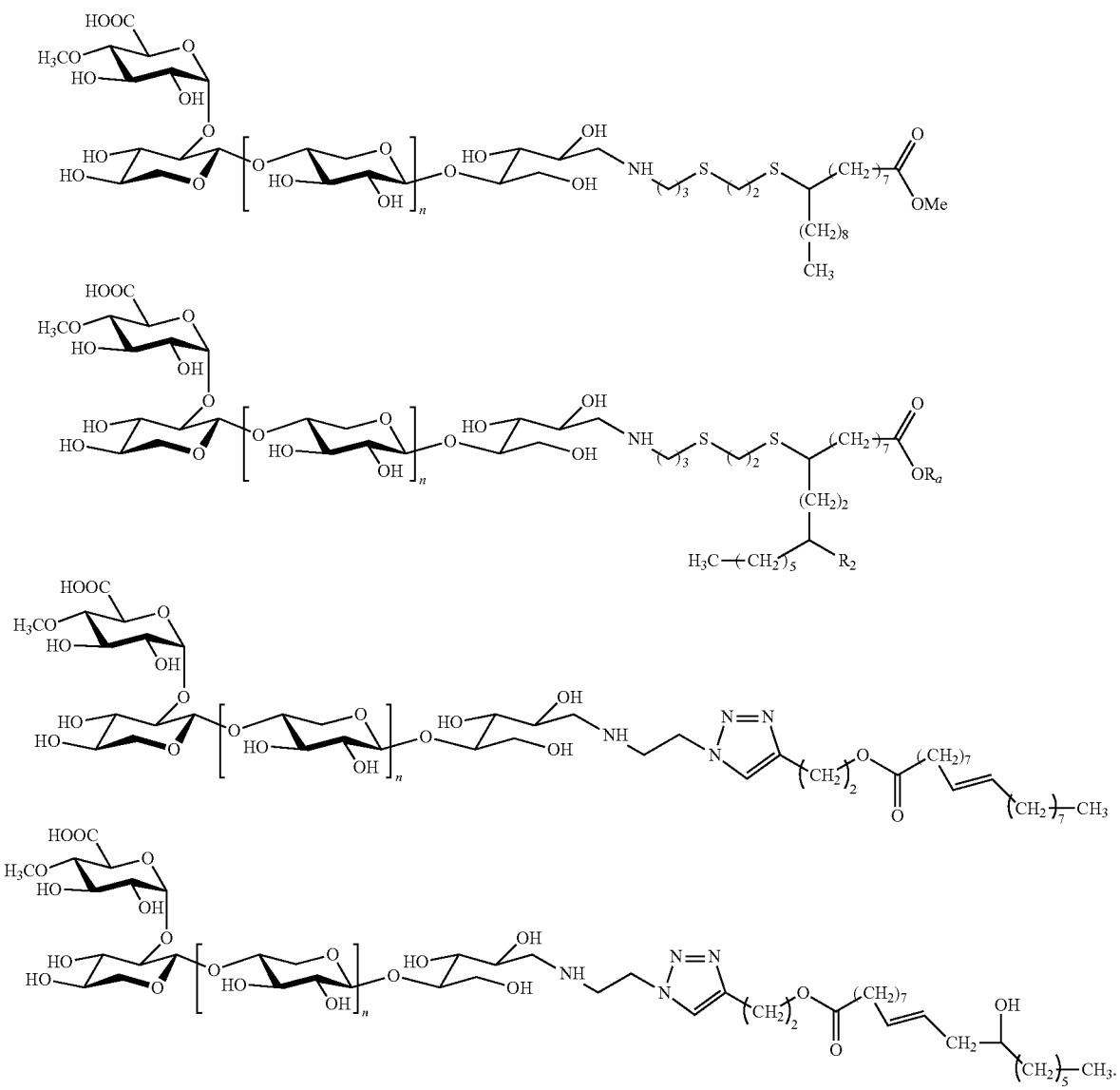

9. A process for the preparation of a compound of formula (I-1) of claim 2, comprising the reaction of a compound of formula (VI):

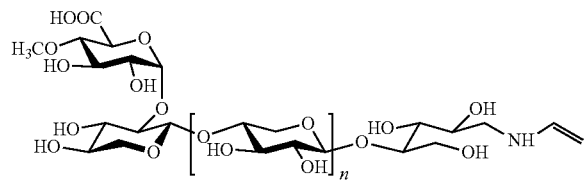

(VI)

with a compound of formula (VII):

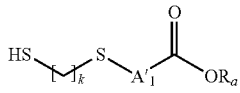

(VII)

k, n, A'$_1$ and R$_a$ being as defined in claim 2.

10. A process for the preparation of a compound of formula (I-2) of claim 3, comprising the reaction of a compound of formula (VIII):

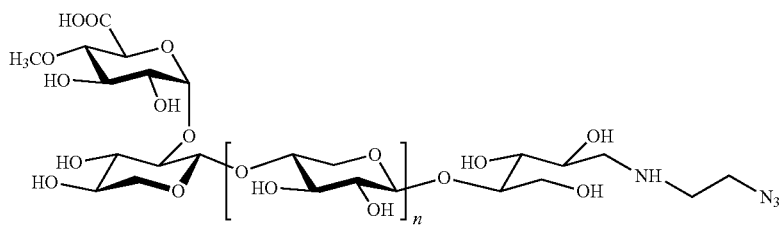

(VIII)

with a compound of formula (IX):

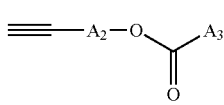

(IX)

n, A$_2$, and A$_3$ being as defined in claim 3.

11. A cosmetic composition comprising at least one compound of formula (I) of claim 1, and a physiologically acceptable vehicle.

12. A pharmaceutical composition comprising at least one compound of formula (I) of claim 1, and a pharmaceutically acceptable excipient.

13. A food supplement comprising at least one compound of formula (I) of claim 1.

14. A surfactant comprising a compound of formula (I) of claim 1.

* * * * *